United States Patent [19]

Johnson, Jr. et al.

[11] Patent Number: 5,314,455

[45] Date of Patent: * May 24, 1994

[54] THERMAL COMPRESS SYSTEM

[75] Inventors: Glenn W. Johnson, Jr., Summit; Henry J. McVicker, Chatham, both of N.J.; K. Donald Shelbourne, Indianapolis, Ind.

[73] Assignee: Aircast, Inc., Summit, N.J.

[*] Notice: The portion of the term of this patent subsequent to Jul. 27, 2010 has been disclaimed.

[21] Appl. No.: 644,835

[22] Filed: Jan. 23, 1991

[51] Int. Cl.⁵ .............................. A61F 7/00
[52] U.S. Cl. .................. 607/104; 607/112; 607/2
[58] Field of Search ............ 128/399, 400, 402, 403, 128/82.1, 40, 24.1, 379, 380, 80 C, DIG. 15, 119.1, 882, 881, 892; 62/530, 259.3; 165/46

[56] References Cited

U.S. PATENT DOCUMENTS

| | | | |
|---|---|---|---|
| 1,732,380 | 10/1929 | Sarason | 128/400 |
| 2,026,747 | 1/1936 | Nemzek | 128/400 |
| 2,832,336 | 4/1958 | Davis et al. | 128/400 |
| 3,584,819 | 12/1970 | Davis et al. | 128/82.1 |
| 3,633,567 | 1/1972 | Sarnoff | 128/DIG. 15 |
| 3,871,381 | 3/1975 | Roslonski | 128/400 |
| 3,901,225 | 8/1975 | Sconce | 128/402 |
| 4,139,004 | 2/1979 | Gonzalez, Jr. | 128/400 |
| 4,338,944 | 7/1982 | Arkans | 128/400 |
| 4,407,276 | 10/1983 | Bledsoe | 128/DIG. 15 |
| 4,628,932 | 12/1986 | Tampa | 128/402 |
| 4,688,572 | 8/1987 | Hubbard | 128/402 |
| 4,872,448 | 10/1989 | Johnson, Jr. | 128/80 L |
| 4,951,665 | 8/1990 | Schneider | 128/400 |
| 4,964,402 | 10/1990 | Grim et al. | 128/402 |

OTHER PUBLICATIONS

Instruction sheet "Aircast Cryo/Cuff Compression Dressings for the Knee and Ankle", Feb. 5, 1990.
Sample instruction sheets for clinical trials entitled "Aircast Cryo/Cuff Knee Compressing Dressing", late 1989, early 1990.
Test result sheet from Methodist Sports Medicine Center, Dr. Shelbourne, Jun. 5, 1990.
"Complications of Arthroscopy and Arthroscopic Surgery: Results of a National Survey", Jesse C. DeLee, M.D., Arthroscopy, vol. 1 #4, 1985, pp. 214–220.
"Pressure Bandaging of the Lower Extremity", Husni et al, JAMA, vol. 206, No. 12, Dec. 16, 1968, pp. 2715–2718.
"Ankle Compression Variability Using the Elastic Wrap, Elastic Wrap with a Horseshoe, Edema II Boot and Air Stirrup Brace", Duffley et al, Athletic Training, Winter 1989, pp. 320–323.

(List continued on next page.)

Primary Examiner—Mark S. Graham
Attorney, Agent, or Firm—Jones, Day, Reavis & Pogue

[57] ABSTRACT

A thermal compress cuff for treating an injured knee has a fluid impervious chamber of flexible material with an upper transverse portion and depending arms extending from the transverse portion. The transverse portion is adapted to encompass a portion of the limb above the knee and the depending arms are adapted to encompass the limb along the sides of the knee and a portion of the limb below the knee while exposing the patella of the knee. The chamber preferably is divided into inner and outer compartments with thermal fluid received by and contained in the inner compartment for abutting contact with the encompassed portion of the limb. An open-cell urethane foam material is contained in the outer compartment for insulating the underlying inner compartment and for enhancing uniform conformance to the limb. The walls of the inner compartment in the distal area of the arms are restrained from movement away from each other so as to restrict expansion of the inner compartment in the arm distal areas and to cause a greater amount of thermal fluid to remain in the proximal arm area and in the transverse portion to lessen venous constriction in the limb below the knee. A hand-held pump is provided for pressurizing the outer compartment to force the inner compartment with the thermal fluid against the areas of the limb being treated. An elastic strap connects the arms around the limb below the knee to minimize venous constriction.

29 Claims, 5 Drawing Sheets

OTHER PUBLICATIONS

"Deep Vein Thrombosis after Elective Knee Surgery", Stringer et al, The Journal of Bone and Joint Surgery, vol. 71-B, No. 3, May 1989, pp. 492–495.

"Knee Pressure Dressings and Their Effects on Lower Extremity Venous Capacitance and Venous Outflow", Mindrebo et al, Methodist Sports Medicine, page #'s and date unknown.

"Effects of Cold and Compression on Edema", Sloan et al, The Physician and Sportsmedicine, vol. 16, No. 8, Aug. 1988, pp. 116–120.

"The Effects of Cold Therapy in the Postoperative Management of Pain in Patients Undergoing Anterior Cruciate Ligament Reconstruction", Cohn et al, The American Journal of Sports Medicine, vol. 17, No. 3, 1989, pp. 344–349.

"Interview of Dr. Kenneth L. Knight", Orthopedic and Sports Medicine News, pp. 1–5, date unknown.

"3K Cryo/Therapy Compression Bandage", Podiatric Products, Jul. 1990, p. 14.

$CP_2$ Therapy, advertisement, 1990, exact date uncertain.

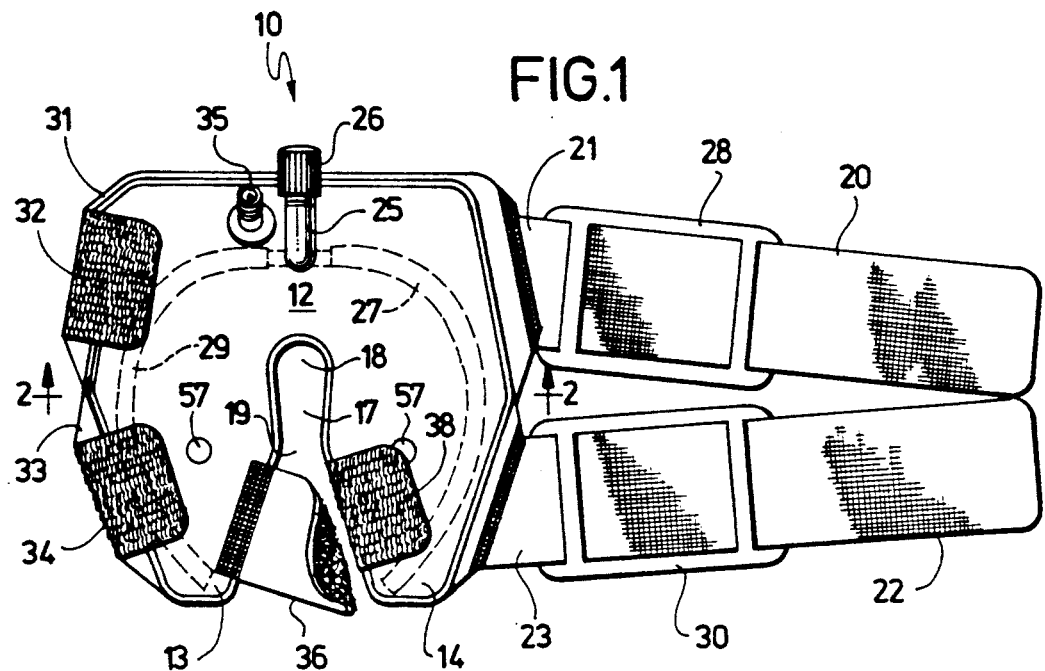
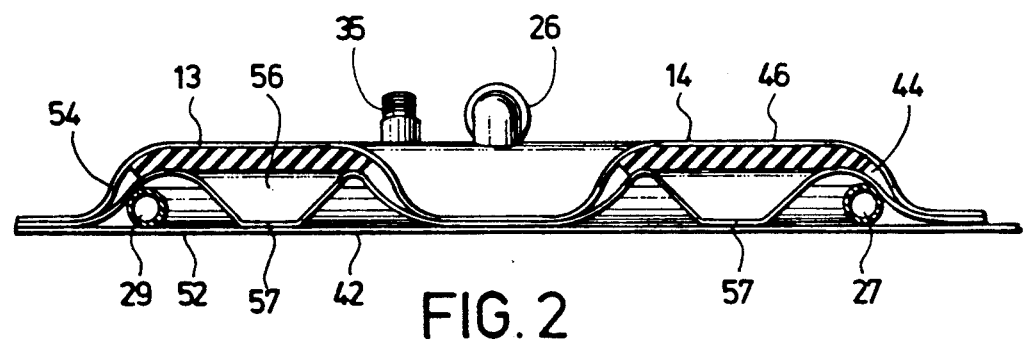

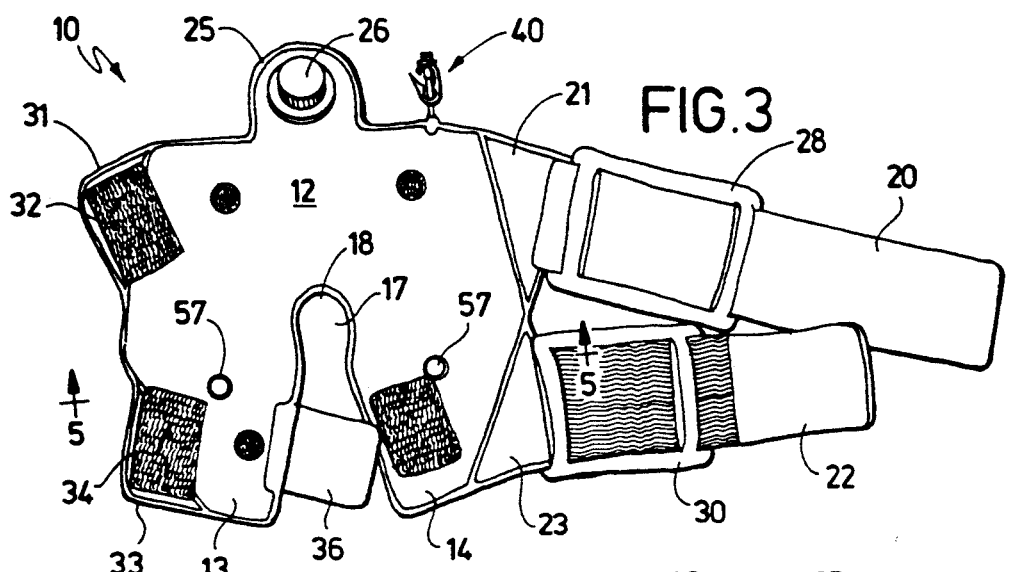
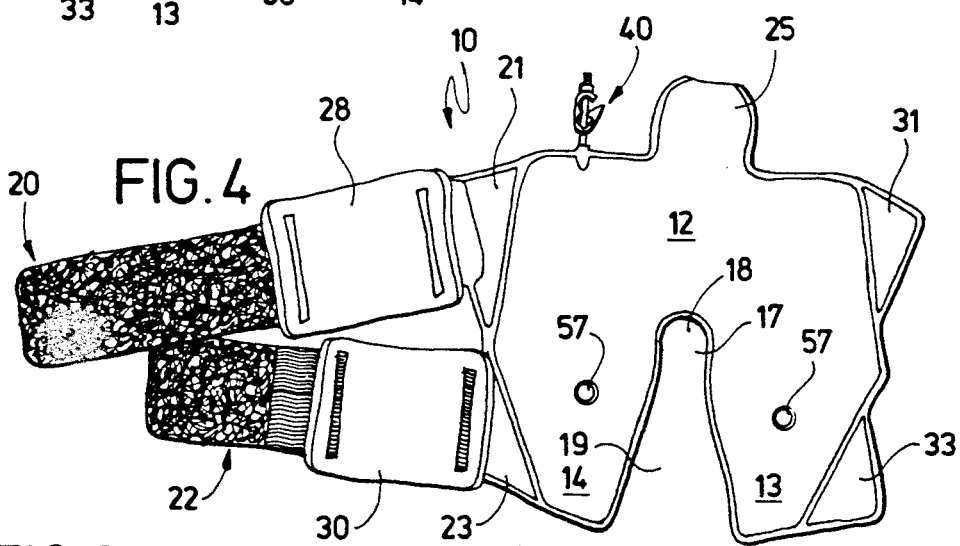
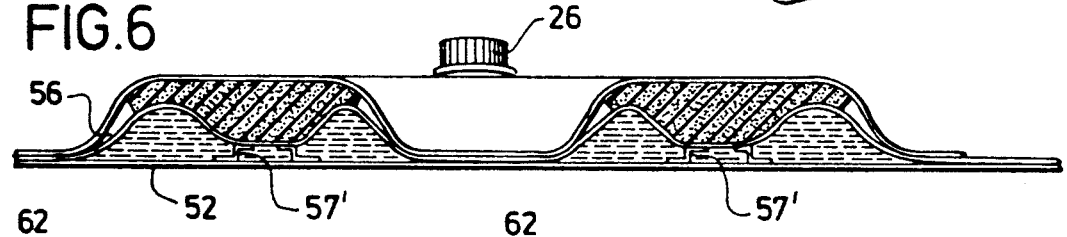
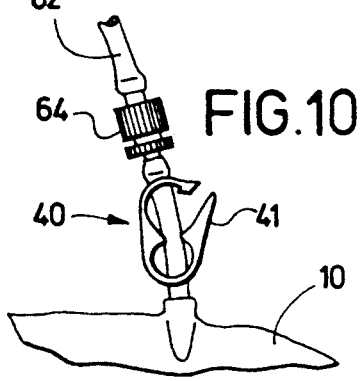
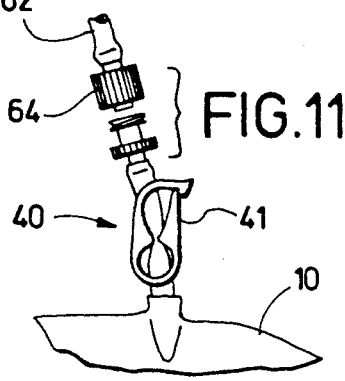

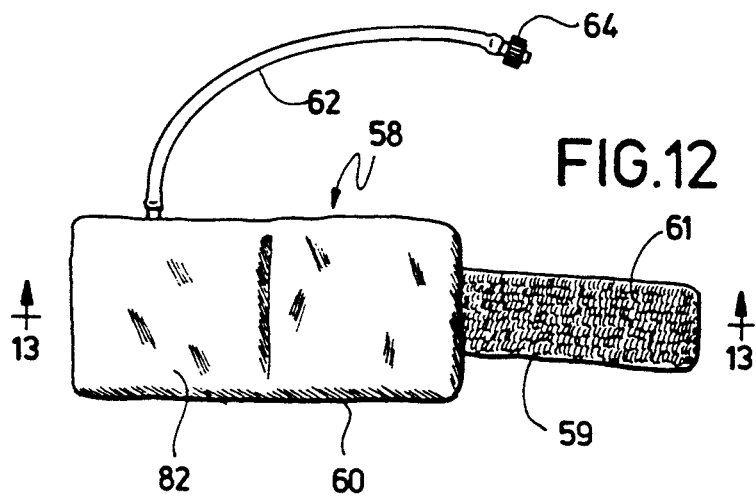
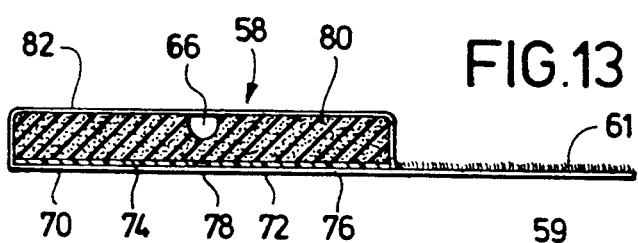
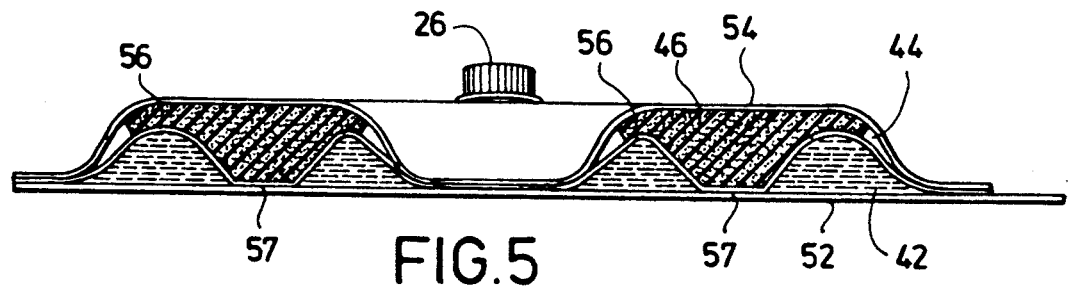
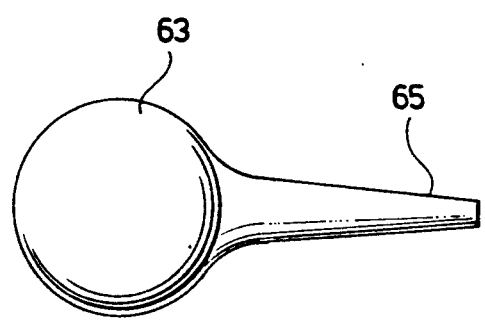

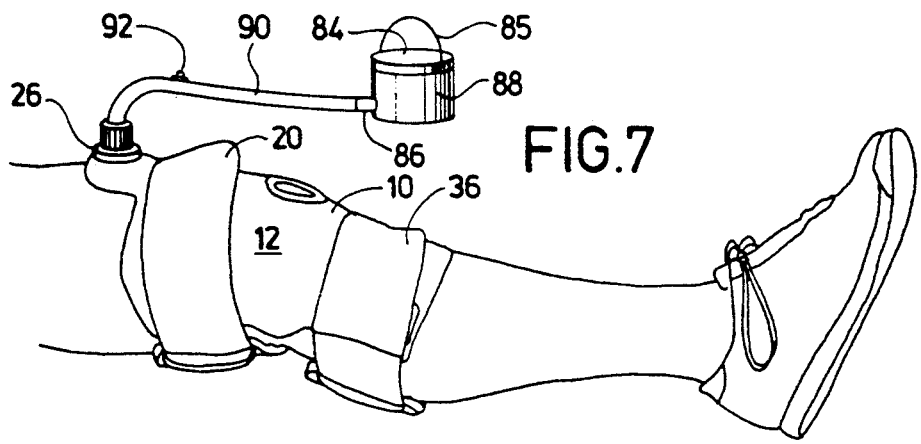
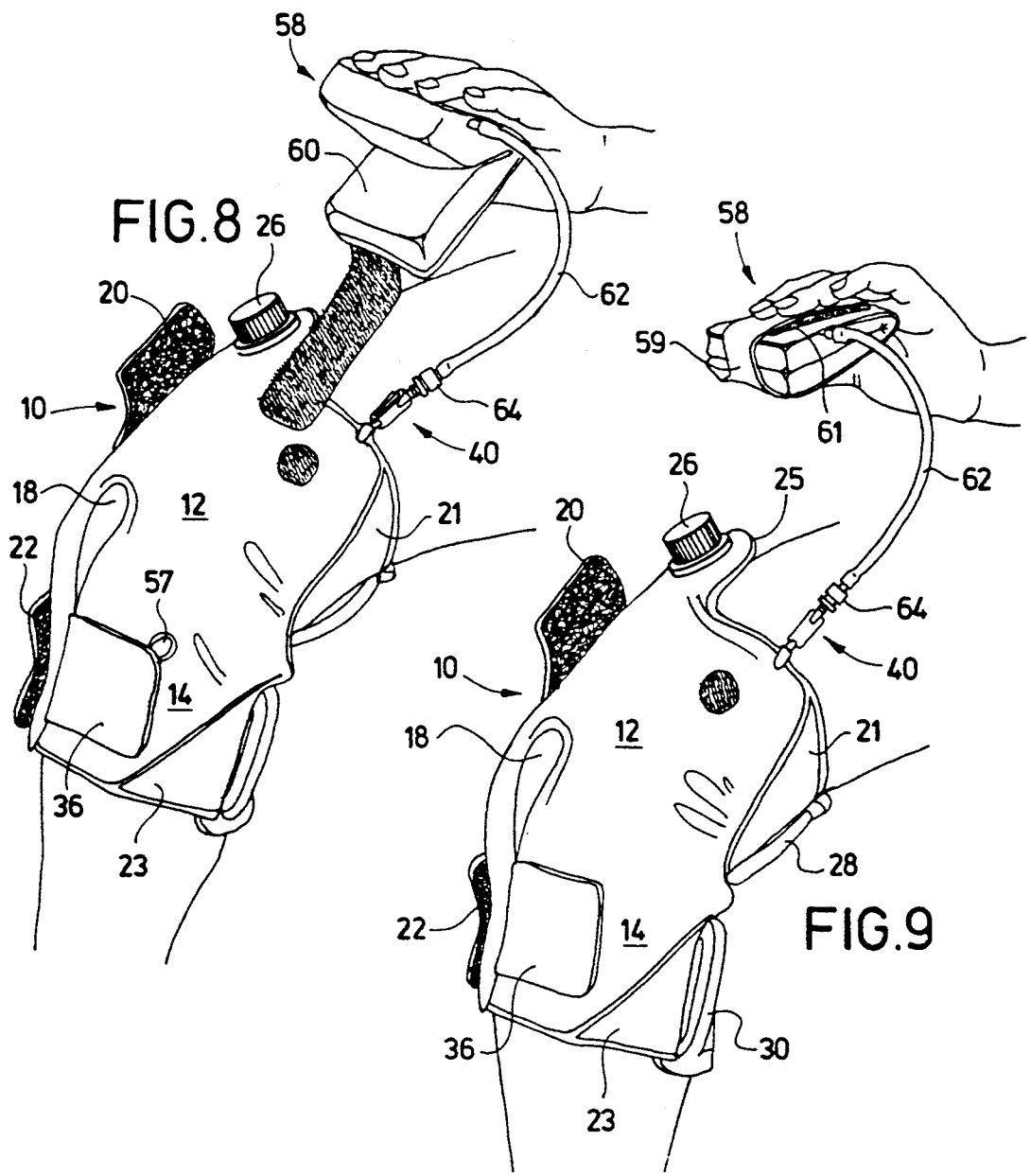

THERMAL COMPRESS SYSTEM

FIELD OF THE INVENTION

This invention relates to systems used in the application of heat or cold and compression to certain injured portions of the human body. In particular, the invention relates to a compress to be fitted around the knee of a human for applying therapeutic compression and cold or heat to the knee in a safer and more effective manner.

BACKGROUND OF THE INVENTION

The therapeutic value of simultaneous application of cold and compression to an injured body part is widely accepted in the medical community, and the acronym RICE for Rest, Ice, Compression, and Elevation, for the primary treatment of injury to joints and limbs of the body, is practiced routinely. After knee surgery, compression and cold are almost universally applied to control the swelling and the commonly occurring hemarthrosis that causes pain and delays rehabilitation. Even so, in a 1983-84 survey by the Committee on Complications of Arthroscopy Association of North America, as published in *The Journal of Arthroscopic and Related Surgery*, Vol. 1, No. 4, 1985, pp. 214-220, postoperative hemarthrosis was seen in 23.5% of all arthroscopies and identified as the most frequently occurring complication.

Modalities for postoperative cold and compression traditionally have been applied separately—compression most commonly by an elastic bandage wrapped around the knee, and the cold by a superimposed plastic bag filled with ice. While this approach appears simple and economical, it has its own complications. In a 1968 study by Husni, et al., reported in *JAMA*, Vol. 206, No. 12, Dec. 16, 1968, pp. 2715-2718, it was demonstrated that an ace wrap applied to the knee at a moderate compression of 20 mm hg retards venous circulation and may contribute to thromboembolism. In a 1989 study of various compression dressings, reported in *Athletic Training*, Winter 1989, pp. 320-323, it was demonstrated that an enormous compression variability existed in the application of an elastic wrap. Four experienced athletic trainers applied wraps to four different ankles four times each. The measured pressures varied from 26 mm to 104 mm hg! While this study was with ankles, it is reasonable to assume that considerable variability must also exist in application of such wraps to the knee.

The risks with this form of compression are suggested by Stringer's 1989 study of "Deep Vein Thrombosis After Elective Knee Surgery", as reported in *The Journal of Bone and Joint Surgery*, Vol. 71-B, No. 3, May 1989, pp. 492-497. DVT was found in 56% of patients after total knee replacement; in 25% of open menisectomies, and in 4% of arthroscopies. In a 1990 study of "Knee Pressure Dressings and Their Effects on Lower Extremity Venous Capacitance and Venous Outflow", by Normal Mindrebo and K. Donald Shelbourne, publication pending, it was determined that, based on the significant changes in venous outflow and venous capacitance, the routine use of the ace wrap as a postsurgical knee dressing should be discouraged.

Numerous other devices have been introduced in recent years for the application of cold and compression, and studies have demonstrated their relative effectiveness. Sloan, et al., in a 1988 study on "Effects of Cold and Compression on Edema", reported in *The Physician and Sports Medicine*, Vol. 16, No. 8, August 1988, pp. 116-120, showed that a Cryopac TM sleeve that applied cold at 15°-20° C. in a cuff inflated to 30 mm hg by Freon gas was highly effective in reducing edema. It was reported in 1989 in *The American Journal of Sports Medicine*. Vol. 17, No. 3, pp. 344-349, that using a Hot Ice Thermal Blanket TM machine to apply cold continuously at 50° postoperatively to the knee significantly reduced pain medication required by the patients. In 1990 there was reported a similar reduction in pain medication in patients using a DuraKold TM dressing consisting of small cells of ice, analogous to a blister pack, in a nylon web support suitable for wrapping around a body part. A 3K Cryotherapy Compression Bandage from Silipos that includes a U-shaped gel filled cooling element in a sleeve that wraps around the entire knee has also been used.

Thus a wide variety of systems have been advanced for the application of compression of cold, and of cold and compression. These include an elastic wrap, the simple ice bag, a freon inflated sleeve, a compressor driven cold water circulating blanket, ice cubes in a strapped-on blanket, and a gel insert in a strapped on sleeve.

But none of these or any other known device has addressed the clearly established need for maximizing the compression and cold in the areas of the knee where needed, while minimizing compression in those areas most sensitive to restriction of venous circulation with its attendant risk of DVT.

This then is the primary object of the present invention. It is to provide a simple and economical device that applies therapeutic cold and a first level of compression to that limited area of the knee that needs the therapy, while using means for controlling the compression below the knee to a second predeterminable amount to minimize the constriction of venous circulation in the lower leg.

To achieve this objective, the present invention includes a cuff with a watertight chamber shaped to envelope only the anterior and sides of the knee, including particularly the suprapatellar pouch. These are the areas where posttrauma body fluids accumulate and where cold and compression are most needed. While the cuff is economically fabricated from sheets of flat material, its novel design permits adjustable shaping so as to conform to the knee even when the knee and cuff are flexed at different angles. The cuff is held in place with an upper proximal strap and a lower distal strap that avoid the popliteal area and minimize constriction. When the cuff is applied to the knee, the straps are secured, but *not tightened*. Then a first amount of compression is applied to the knee by inflating the cuff to a reasonably predeterminable amount, which causes the chamber to expand. The expansion tensions the straps and applies compression to the areas of the knee under the chamber.

As an important element of the invention, the expansion of the cuff from inflation becomes greater in the area above the patella (where swelling is greatest) and the expansion is restricted in the area below the patella (where swelling is less). This causes the distal strap to be tensioned to a lesser degree than the proximal strap. It is well known medically and tests demonstrate that venous flow is far more sensitive to constriction in the region of the distal strap and less sensitive in the thigh under the proximal strap. Thus, by limiting tightening of the distal strap, little or no pressure is applied below the knee or in back of the knee and constriction of venous flow is further minimized.

The inflation of the cuff can be achieved by either of two means. In the preferred form of the invention, the cuff is strapped in place when empty and is then inflated with ice water which is supplied by a tube from a container that is elevated above the cuff and pressurized by gravity—a method similar to that disclosed as a Gravity Thermal Dilator in U.S. Pat. No. 2,026,747. With this technique the amount of compression is determined by the elevation of the container e.g.,—15"=28 mm hg.

In an alternative form, the cuff is divided into two coextensive chambers. The inner chamber is filled with ice and water before application to the knee. When the cuff is in place and the straps secure (but not tight), the outer chamber is inflated by a hand-held pump or bulb, in a manner somewhat similar to that disclosed in Davis's Thermal Pressure Splint, U.S. Pat. No. 3,548,819. The amount of inflation (and compression on the knee) can then be observed with a pressure indicating device such as that described in commonly assigned copending application Ser. No. 07/502,806, incorporated by reference herein in its entirety, or by the extension bellows type gauge herein disclosed.

The unique effectiveness of the present invention in limiting constriction of venous circulation while applying effective compression to the knee can be demonstrated using a technique similar to pneumatic plethysmography. The lower leg is elevated about 12" above the hip, and a pneumatic cuff is fastened around the calf and inflated to a consistent base-line pressure. Three pneumatic pressure probes are attached to the knee to measure pressure above the patella, under the proximal strap and under the distal strap. A compression dressing such as an ace wrap or the dressing of the present invention is applied to the knee and compressed to a predetermined effective level, such as 28 mm hg. If the dressing constricts venous flow the calf will swell from the trapped blood and pressure in the cuff will rise. Greater swelling means greater venous constriction and greater risk.

In highly repeatable tests it has been found that when an ace bandage is wrapped on the knee to a pressure of 28 mm hg, the calf will swell by about 20 mm hg above base line. But when the dressing of the present invention is applied as specified and inflated with water to the same pressure at the knee, the calf pressure rises insignificantly, by about 2 or 3 mm hg. Thus, the present invention applies little or no pressure below the knee and no pressure in back of the knee.

The reason for this difference can be seen by the pressures measured at the back of the knee under the straps (or at the same location with the ace bandage). With the ace wrap (and all known devices that envelope the knee) the pressures around the knee are generally uniform. Proximal and distal pressures at the back of the leg are the same as above the patella. With the present invention, the pressure under the proximal strap is at one level; however, under the distal strap the pressure is significantly lower, typically only 55% or 60% as high as under the proximal strap and there is no pressure on the popliteal area (the back of the knee).

In an additional test, a cuff was constructed as a complete cylinder completely enveloping the knee, similar to that disclosed by Cryomed. When inflated with water to the same 28 mm hg pressure at the knee, the calf pressure swelled by about 17 mm—an amount comparable to the swelling with an ace wrap, and far greater than with the present novel device.

A further advantage with the invention developed herein is the ease with which compression can be periodically reduced without removing the dressing or adjusting the straps. With the preferred embodiment, the water from the cuff is routinely recycled back to the cooler for rechilling by lowering the cooler below the cuff. During the two minutes or so required for rechilling the water, the pressure in the cuff falls to zero. This permits even any minimal pooling of blood that might occur in the veins to be flushed out. Similarly, in the pneumatically pressurized embodiment the pressure can easily be dropped periodically, without disturbing the straps or rewrapping the dressing, as with conventional devices.

The medical effectiveness of earlier version of the present invention through pre-market clinical trails found that hemarthrosis can be minimized, and pain reduced, by early and extended use of this type of compression dressing. The ideal postoperative knee dressing would improve patient comfort, minimize intra-articular hemarthrosis and have a minimal effect on deep vein hemodynamics.

Thus, it is an important aspect of the present invention to provide a dressing with a watertight chamber for application of pressure and cold to the knee that covers only about the anterior half of the knee, avoids the popliteal area, and is held in place by a pair of adjustable straps at the proximal and distal margin, with means for inflating and thereby expanding the dressing so as to apply compression to the knee after the straps are secured without, or with minimal, tensioning.

The invention also provides means for relatively restricting the expansion of the dressing in the distal area so as to limit tensioning of the distal strap in order to lessen venous constriction. In the preferred embodiment disclosed herein, the restricting means is accomplished by tethering or spot-welding the layers of the dressing watertight chamber in the distal area.

Also, in the preferred embodiment, the novel device has a proximal strap that is inelastic and a distal strap that is elastic to further limit distal constriction.

The invention includes a closed cycle pressurization means that uses chilled water from an elevated container that is connected by a tube to the watertight chamber of the device. By raising the container above the knee, the chilled water pressurizes the device and, when the water is warmed by the body, by lowering the container below the knee, the water is returned from the device to the container for recooling. Alternatively, a compartment of the device may be inflated with air by a novel pump or by a bulb.

The invention is fabricated from sheets of flat material, but the novel design permits adjustable shaping of the invention so as to conform to the knee even when the knee is flexed at different angles.

The novel invention also includes a syphon in the closed chilled water system that permits draining the water from the device without removing the cuff.

SUMMARY OF THE INVENTION

Thus, the present invention relates to a device for treating an injured knee, comprising means for applying therapeutic cold and compression only to the general area of the suprapatellar pouch and to the general area alongside the knee, means coupled to the compression applying means for limiting compression applied to the general area alongside the knee while simultaneously allowing a predetermined greater compression to be applied to the general area of the suprapatellar pouch, and means for attaching the cold and compression applying means to the knee. The device comprises a fluid impervious chamber of flexible material having an upper transverse portion and depending arms extending from the transverse portion. The transverse portion is adapted to encompass a portion of the thigh above the knee in the general area of the suprapatellar pouch, and the depending arms are adapted to encompass the limb in the areas generally along the sides of the knee and a portion of the limb below the knee while exposing the patella. The chamber is adapted for receiving and containing a thermal fluid for abutting contact with the encompassed portion of the limb. An adjustable length inelastic strap extends under the thigh from one end of the transverse portion to the other end for holding the transverse portion of the chamber in encompassing engagement with the general area of the suprapatellar area above the knee. An elastic strap extends under the limb from one of the depending arms to the other depending arm to adjust their position with respect to each other while a third adjustable length strap, either elastic or inelastic, extends over the top of the limb from inside of one of the depending arms to the inside of the other depending arm to hold the arms securely against the limb.

The invention also includes the fluid impervious chamber being divided into inner and outer compartments, each having an outer wall and a common wall. The inner compartment is adapted for receiving and containing a thermal fluid and can be placed in abutting contact with the encompassed portion of the limb being treated. Open-cell urethane foam material is provided in the outer compartment to insulate the underlying inner compartment, to minimize sweating of the outer compartment in humid climates and to maintain the shape of the device while permitting conformation of the device to encompass the person's limb. Selectively closable means is attached to the outer compartment for permitting a fluid to be introduced therein sufficient to force the inner compartment with its thermal fluid in pressure engagement with the encompassed portion of the limb. The expansion of the inner chamber in the distal area of the arms is restricted, thereby to cause a greater amount of thermal fluid to reside in the proximal area and allow less thermal fluid in the distal area of the inner chamber, resulting in greater compression in the proximal area and less in the distal area. In this manner less venous constriction occurs in the leg below the knee.

BRIEF DESCRIPTION OF THE DRAWINGS

These and other objects of the present invention will be more fully understood in conjunction with the accompanying drawings in which like numerals represent like elements and in which:

FIG. 1 is a top plan view of the preferred embodiment of the novel pressure cuff;

FIG. 2 is a cross-sectional view of the cuff shown in FIG. 1, taken in the direction of the arrows 2—2;

FIG. 3 is a top plan view of an alternate embodiment of the novel pressure cuff;

FIG. 4 is a bottom plan view of the pressure cuff of FIG. 3;

FIG. 5 is a cross-sectional view of the embodiment of the thermal compress shown in FIG. 3 along the line 5—5 illustrating spot welding to hold the wall of the inner compartment together in predetermined areas;

FIG. 6 is a cross-sectional view of an alternate embodiment of the thermal compress at the same section as 5—5 and illustrating tethers that hold the walls of the inner compartment in spaced relationship;

FIG. 7 is a diagrammatic representation of the novel pressure cuff placed about the knee of an extended leg;

FIG. 8 is a view of the novel device placed on a flexed knee with one form of air pump attached thereto;

FIG. 9 is a view of the novel thermal compress placed on a flexed knee with the air pump attached thereto and folded after the compress has been inflated;

FIG. 10 is a side view of the compress quick disconnect in its connected relationship with the air pump hose;

FIG. 11 is a side view of the compress quick disconnect after being disconnected from the air pump hose;

FIG. 12 is a top view of one embodiment of the portable air pump used to pressurize the thermal cuff; and FIG. 13 is a cross-sectional view of the air pump taken along lines 13—13 of FIG. 12;

FIG. 14 is a side view of a bulb-type pump that may be used to pressurize the thermal cuff;

DETAILED DESCRIPTION OF THE DRAWINGS

Figure 15:
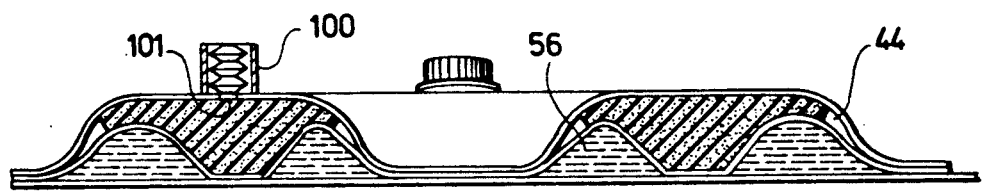
FIG. 15 is a cross-sectional view of a thermal cuff with a pressure gauge thereon.

While the novel thermal compress of the present invention can be used to apply cold or hot temperatures to the human body, it will be described herein with respect to providing a cold temperature where its greatest use is anticipated. As can be seen in FIG. 1 and FIG. 2, the preferred embodiment of the novel thermal compress device or cuff, designated generally by the numeral 10, is designed to be applied to the knee of the leg of an individual. The cuff 10 has an upper transverse portion 12 and lower depending arms 13 and 14 extending from the upper portion 12. The cuff 10 can be wrapped about the knee portion of a leg. The opening designated by the numeral 18 in the cuff 10 is intended to receive the knee cap or patella as will be shown hereafter. In this way, the pressure and temperature are not applied to the patella or kneecap of the person wearing the compress. A proximal strap 20 and a distal strap 22 are attached to thermal compress cuff 10 at tabs or wings 21 and 23, respectively, on arm 14. Strap 22 is made of any well-known flexible material having a portion with a fastening material thereon known as Velcro. Strap 20 is made of a relatively inelastic material. Straps 20 and 22 are arranged for attaching relationship with mating Velcro strips 32 and 34 mounted on opposing tabs or wings 31 and 33, respectively, on arm 13 of thermal compress cuff 10. Further, the straps 20 and 22 have resilient foam attachments 28 and 30 attached respectively thereto for the purpose of providing a cushion for the underside of the person's leg to which the thermal compress cuff 10 is attached. A neck 25 has a closable opening 26 therein for admitting the cold liquid to the interior of the cuff 10.

It will be noted that the cuff 10 is bifurcated beginning with opening 18, thus separating depending arms 13 and 14. This permits adjustment for knee angle and width. The gap between the arms 13 and 14 includes a truncated triangular gap 19. The gap 19 changes the profile of the applied cuff 10 from flat to conical for better conformation of the arms 13 and 14 to the leg when the knee is in the flexed position. Velcro fastener 34 and elastic strap 22 connect the depending arms 13 and 14 together under (or behind) the leg while strap 36 and mating Velcro strip 38 connect the arms 13 and 14 together over the top of the leg. Thus the upper (proximal) and lower (distal) straps 20 and 22 are placed so as to avoid the popliteal area of the knee and minimize constriction thereof. This construction permits bending adjustment of the cuff for different degrees of flexation of the knee from full extension to about 30°. The arms 13 and 14 could be fixed permanently to each other with flexible connectors without providing for adjustment if desired. The use of the flexible and elastic strap 22 under the leg tends to limit the constriction of the leg below the knee and thus minimizes venous constriction below the knee which is desirable during treatment of the knee by use of the cuff 10.

FIG. 2 is a cross-sectional view of the novel cuff. As can be seen in FIG. 2, the device 10 includes a fluid impervious chamber formed so as to be divided into inner and outer generally coextensive compartments 42 and 44, respectively. Compartment 42 has an outer wall 52 and compartment 44 has an outer wall 54. Each of the compartments 42 and 44 has a common inner wall 56. The inner compartment 42 is adapted for receiving and containing the thermal fluid in a desired temperature range in generally uniform and abutting contact via wall 52 with the encompassed portion of the leg being treated. A Y-shaped internal syphon having tubes 27 and 29 connects to neck 25 and closable opening 26 for filling and draining the fluid from inner compartment 42. Draining is important for rechilling the fluid warmed during extended therapy. Tubes 27 and 29 are formed of a material such as plastic and are approximately 5/16" on the inside diameter. They extend from the fill opening 26 to the distal end of each of the arms 13 and 14 as shown in phantom lines in FIG. 1. Thus, even though the fill port 26 is at the top of the compress, all of the fluid can be completely drained from the bottom.

An open-cell urethane foam material 46 approximately 0.30" thick that will compress to about half its normal thickness under a 1 psi load is suitable for use in outer compartment 44 for insulating the underlying inner compartment 42, for minimizing sweating of the outer compartment 44 and for maintaining the shape of the cuff 10 while permitting conformation of the cuff 10 while encompassing the person's leg.

When the cuff 10 is used, the proximal strap 20 and distal strap 22 secure the cuff to the leg snugly but not tightly as described earlier. The cuff may be pressurized with a fluid from an elevated container using a closed cycle system.

As shown in FIG. 7, a cooler or container 88, which may be either a flexible pouch or a rigid container, holds a fluid such as ice and water sufficient for six to eight hours of cryotherapy. The cooler 88, if a rigid container, has a lid 84 and a handle 85 and is coupled by a hose 90 to the connection 26 on the cuff 10. After the cuff 10 is applied to the limb, the cooler 88 is elevated above the limb as illustrated in FIG. 7 and the ice chilled water flows into the cuff 10. Compression of the limb, due to the gravity flow of the ice water, is proportional to the elevation of the cooler 88 with respect to the cuff 10. A manually operated valve 92 allows the flow of ice water to be stopped when the desired pressure is reached by manually closing the valve. Thus, the pressure is sealed in the cuff and skin temperature falls rapidly. After 15 to 30 minutes, body heat will warm the water in the cuff 10. The water is then "rechilled" by reversing the cycle. The cooler is lowered below the leg and the valve 92 is opened. The warmed water is drained by the syphon system back into the cooler 88. After a short interval allowing mixing of the water with the ice, the cooler 88 is again elevated and the cuff-filling process repeated. Thus, a closed chilled water system is used and the water is recirculated between the container and the cuff in the closed system to maintain the water at the desired temperature. As pointed out previously, it will be noted in FIG. 1 that the Y-shaped internal syphon tubes 27 and 29 extend to the distal areas of the inner compartment 42 of arms 13 and 14, thus either draining the warm water from or filling the compartment with cold water as set forth above. When filling the inner compartment 42 with cold water, the vent 35 (FIGS. 1 and 2) may be opened to allow air to escape as the chilled water is entering the compartment 42.

As thermal fluid fills the inner compartment 42, it expands the cuff 10, compresses the limb 16 and tightens the straps 20 and 22. Normally, the cuff 10 would expand uniformly and both straps would be similarly tensioned around the upper and lower limb. Because most of the swelling after knee surgery takes place in the suprapatellar pouch—immediately above the knee, it is medically desirable to have more cold and compression in the proximal area above the patella and less in the distal area covered by the arms 13 and 14. Additionally, the risk of undesirable constriction is greater under the distal strap below the knee.

In order to provide more cold fluid to the proximal area and less constriction in the distal area, the present invention includes means to restrict the amount of expansion of the fluid compartment in the distal area of the cuff or compress 10 but not in the proximal area. This causes more fluid to remain in the upper area 12 and less in the arms 13 and 14. This results in less tightening of the lower strap 22.

This novel result is accomplished by both placing an elastic strap 22 below the knee, as indicated previously, and also by holding the two walls 52 and 56 of the distal portion of compartment 42 in fixed relationship to each other so as to constrict expansion of the chamber 42 in the depending arms 13 and 14.

The simplest and preferred manner of accomplishing this is to spot weld the two sides 52 and 56 of the chamber in the area 57 of the distal portion of arms 13 and 14, similar to the manner of a quilt, as illustrated. (See FIGS. 2 & 5). An alternative is to weld a short tethering strap 57' to each internal surface 52 and 56 as shown in FIG. 6, to permit some but limited expansion in the immediate area. Tests show that pressure under the distal strap 22 is reduced by about a third by this dual technique of an elastic strap and restricted expansion of the chamber.

In the preferred embodiment, the outer compartment 44 contains foam 46 that overlies the thermal fluid-filled compartment 42. The foam-filled outer compartment 44 performs two functions. First, it insulates the underlying cold fluid compartment 42, thereby maintaining the cold temperature for a longer period of time while preventing sweating of the cuff upper surface 54. Second, it maintains the shape of the cuff 10 while permitting conformation of the cuff around the leg and it reduces sagging of the device under the weight of the fluid. The foam may be an open-cell urethane foam about 0.30 inches thick that will compress to about half its normal thickness under a 1 psi load.

In another embodiment, external compression is used to cause the outer wall 52 of the cold fluid compartment 42 to more uniformly engage the body area being treated. This is accomplished by applying a pressurized fluid such as air through a selectively closable opening 40 shown in detail in FIGS. 9-11. The selectively closable opening 40 (as shown in FIG. 3) is attached to the outer compartment 44 for permitting pressurized fluid such as air to be introduced therein sufficient to force the inner compartment 42 with its thermal fluid in pressure engagement with the encompassed portion of the leg. This increases the pressure in the foam-filled chamber 44.

One form of a pump that may be coupled to orifice 40 for applying the supplemental pressure is illustrated in FIGS. 8, 9, 12 and 13. The pump is designated generally by the numeral 58. It has a rectangular body portion 60 to which is attached a strap 59 having a Velcro strip 61 thereon. A hose 62 extends from body portion 60 to carry the compressed air to opening 40 in the outer compartment or chamber 44 of the inflatable cuff. The unit may be folded about center section 66 and Velcro strap 59 wrapped around the open end of the air pump 58 to have mating contact with a second Velcro strip 70 (FIG. 13) on the obverse side of the pump 58.

A cross section of the novel pump is shown in FIG. 13. The pump 58 is actually an air foam cell that is approximately six inches long and two inches wide and has strap 59 attached therewith with the Velcro strip 61 thereon. The lower portion 72 is an air impervious resilient material such as plastic and has attached thereto first and second substantially rigid surfaces 74 and 76 which may be, for instance, thin, rigid plastic layers. Plastic layers 74 and 76 are separated from each other by a small gap 78. A cellular foam layer 80 has a portion removed to form an indentation 66 and allow the foam cell to be easily folded about the indentation. An outer pliable surface 82 such as this plastic is placed over the foam 80 and sealed to the lower plastic surface 72 to form an airtight compartment. Hose 62 communicates with the inside of the airtight compartment. When the air cell is folded about separation 78 and indentation 66 as shown in FIGS. 8 and 9, the entrapped air in the cell is forced out via tube 62 and orifice 64 into the cuff 10 as shown in FIG. 10. By clamping the selectively closable opening 40 with quick disconnect clamp 41, the hose 62 may be disconnected from orifice 64, as shown in FIG. 11, and the air cell 58 will expand to its straight configuration as in FIG. 12. In this process the cell 58 accumulates air through hose 62 to the interior thereof. The hose 62 can then again be coupled to the cuff 10 to add additional air as needed when the air cell 58 is again folded. Alternatively, a one-way valve may be coupled to the cell to allow air in but not out. Thus, the hose 62 would not have to be disconnected from the orifice 64. Typically, with the cuff 10 used as illustrated in FIGS. 8 and 9, only one pressurization cycle of the pump 58 is required to sufficiently pressurize the cuff 10. When the pump 58 is not in use, it may be disconnected from the cuff 10 and folded as illustrated in FIG. 9 with the strap 59 passing around the open end of the pump and the Velcro strip 61 thereon cooperating with the Velcro strip 70 on the bottom of the air cell 58 to hold the pump in the closed shape as shown.

Alternatively, for more variability of pressurization, a bulb 63, as shown in FIG. 14 and well known in the art, may be used to pressurize the outer compartment 44. The end 65 of bulb 63 may be inserted in a hose such as hose 62 or directly in connector orifice 40 to pressurize outer compartment 44.

Figure 16A:
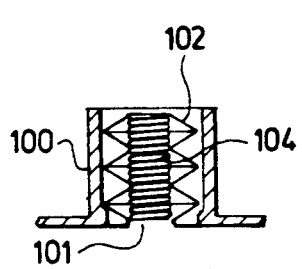
FIGS. 16A-16D are cross-sectional views of the pressure gauge in its various positions to indicate pressure in the thermal cuff compartments.
Figure 16B:
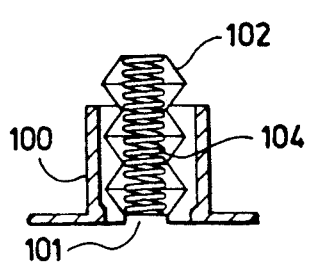
Figure 16C:
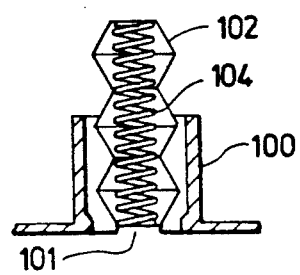
Figure 16D:
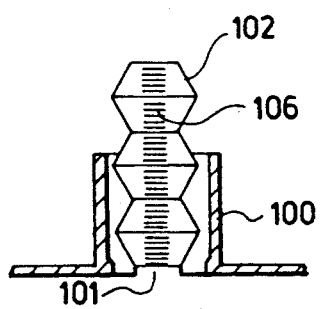

FIG. 15 is a cross-sectional view of the novel cuff in which a gauge means housing 100 has been placed to indicate the pressure in the outer compartment 44 so as to prevent over inflation. The gauge means housing 100 may include an expandable bellows 102 such as shown in FIG. 16A (where it is entirely compressed) in communication with chamber 44 via aperture 101. The bellows 102 is held in place with no pressure in compartment 44 by resilient means such as a spring 104. As pressure is increased in the outer compartment 44, the bellows 102 begins to expand against the force of spring 104 and protrudes from the housing 100 as illustrated in FIG. 16B. As pressure in compartment 44 continues to increase, the bellows 102 becomes fully extended as illustrated in FIG. 16C. The bellows may have markings 106 thereon as shown in FIG. 16D to indicate the amount of pressure within compartment 44. The marks 106 may simply be reference points to enable the user to adjust the same pressure in the compartment 44 each time the thermal compress is used.

Thus, a novel thermal compress cuff has been disclosed which is adapted to encompass a knee of a person. It has a substantially fluid impervious chamber formed of flexible material having an upper portion and depending arms extending from the upper portion. The chamber is divided into inner and outer compartments each having an outer wall and a common wall. The inner compartment is adapted for receiving and containing a thermal fluid and is in abutting contact with the encompassed portion of the person's knee. An opening is formed in the inner compartment for receiving a thermal fluid through a hose from an external container. As the container is lifted above the knee, the thermal fluid is under pressure and pressurizes the inner compartment to an amount corresponding to the height of the container above the knee. Open-cell urethane foam in the outer compartment insulates the underlying inner compartment thus minimizing sweating of the outer compartment in humid climates. It also maintains the shape of the device while permitting conformation of the device encompassing the person's limb.

In another embodiment, a selectively closable opening is attached to the outer compartment for permitting pressurized fluid to be introduced therein sufficient to force the inner compartment with its thermal fluid in pressure engagement with the encompassed portion of the knee. Means for restricting expansion of the cavity in the distal area of the arms is provided to cause a greater amount of thermal fluid to remain in the proximal area (providing more pressure) and allow less thermal fluid in the distal area of the arms. A novel portable air cell is provided to pressurize the cuff as needed.

In keeping with the foregoing, it will be understood that, for example, the container 88 (FIG. 7), may be connected directly to neck 25 (FIG. 1) via a quick disconnect such as the type made by Colder Fittings (Model Nos. PLCD 170-06 & PLCD 220-06). It also should be understood that neck 25 and opening 26 may be made large enough to permit the direct introduction of ice cubes and water in lieu of a separate container 88.

Similarly, the outer compartment 44 may be inflated orally by a tube connected to orifice 40.

While the invention has been shown and described with respect to a particular embodiment thereof, this is for the purpose of illustration rather than limitation; other variations and modifications of the specific embodiment herein shown and described will be apparent to those skilled in the art all within the intended spirit and scope of the invention. Accordingly, the patent is not to be limited in scope and effect to the specific embodiment shown and described nor in any other way that is inconsistent with the extent to which the progress in the art has been advanced by the invention.

We claim:

1. A thermal compress device adapted to encompass at least a portion of a limb of a person and comprising:

a substantially fluid impervious chamber of flexible material having an upper transverse portion and a pair of spaced arms having distal ends, said arms depending from the upper portion, said upper transverse portion for contacting the general area of only the suprapatella pouch and the depending arms contacting substantially only the respective sides of the knee, said chamber being divided into inner and outer fluid tight compartments, each having an outer wall and a common wall;

means forming part of said chamber for restricting expansion of the inner compartment in the distal area of the arms to cause a greater amount of thermal fluid to remain in the transverse portion area for greater compression and to allow less thermal fluid in the distal area of the arms, for less compression thereby to lessen venous constriction below the knee;

the inner compartment adapted for receiving and containing a thermal fluid of a desired temperature and for abutting contact with the encompassed portion of the person's limb;

resilient material in the outer compartment for insulating the underlying inner compartment and for maintaining the shape of the device while permitting conformation of the device to the person's limb; and selectively closable means attached to the outer compartment for permitting pressurized fluid to be introduced therein sufficient to force the inner compartment with its thermal fluid in pressure engagement with the encompassed portion of the human limb.

2. A thermal compress cuff for treating an injured knee of a limb, said cuff comprising:

a fluid impervious chamber formed of flexible material having a transverse portion and a pair of arms having distal ends, said arms depending from the transverse portion, the transverse portion adapted to encompass substantially a portion of the limb above the knee and the depending arms adapted to encompass at least a portion of the limb along the sides of the knee and a portion of the limb below the knee, said arms being separated to expose the patella of the knee;

said chamber being adapted for receiving and containing a thermal fluid for treatment of said knee and for abutting contact with the encompassed portion of the limb;

first means for holding the transverse portion of the chamber in encompassing engagement with substantially only the portion of the limb above the knee so as to allow some constriction of the limb above the knee;

second means for holding the depending arms of the chamber in encompassing engagement with at least a portion of the limb along the sides of and below the knee with the patella being positioned between the depending arms so as to limit constriction of the leg below the knee to an amount less than the constriction above the knee; and means independent of the first and second holding means associated with said chamber for applying pressure to the fluid in the chamber.

3. A thermal compress cuff as in claim 2 further comprising:

a common wall dividing the chamber into inner and outer compartments;

means coupled to the interior of the inner compartment for supplying a thermal fluid thereto, the inner compartment being adapted for abutting contact with the encompassed portion of the limb; and a resilient material contained in the outer compartment for insulating the underlying inner compartment and for maintaining the shape of the cuff while permitting conformation of the cuff to the encompassed limb.

4. A cuff as in claim 3 wherein said resilient material is an open-cell urethane foam material.

5. A thermal compress cuff as in claim 3 further including a quick disconnect selectively closable means attached to said outer compartment for permitting pressurized fluid to be introduced therein sufficient to force the inner compartment containing thermal fluid in pressure engagement with the encompassed portion of the human limb.

6. A thermal cuff as in claim 3 further including means in said compartment for restricting expansion of the inner compartment in the distal area of the arms to cause a greater amount of thermal fluid to remain in the transverse portion of the cuff and to allow less thermal fluid in the distal area of the arms.

7. A thermal cuff as in claim 2 wherein said first means for holding the transverse portion of the flexible material forming the chamber in encompassing engagement with the portion of the limb above the knee comprises:

an elongated inelastic strap attached to one end of the transverse portion of the flexible material for passing under the limb above the knee; and means for releasably receiving the elongated inelastic strap in a fastening relationship to hold the transverse portion of the flexible material in engagement with the limb above the knee and to enable the elongated inelastic strap to be properly positioned under the limb above the knee.

8. A thermal compress cuff as in claim 6 wherein the means for restricting expansion of the chamber in the distal area of the arms comprises means in the distal area of each arm coupling wall of the inner compartment to each other in at least one location to limit the distance the inner compartment walls can move apart.

9. A thermal compress device as in claim 8 wherein the inner compartment walls are attached to each other by a single tether strip in at least one location to permit restricted expansion of the inner compartment walls in the area of the tether.

10. A thermal compress device as in claim 8 wherein the inner compartment walls are attached to and touching each other at a single spot, as by spot welding, to prevent any expansion of the inner compartment walls in the area of the spot weld.

11. A thermal compress device as in claim 3 further comprising gauge means coupled to the interior of the outer compartment for indicating the fluid pressure in the compartment.

12. A thermal compress cuff as in claim 11 wherein said gauge means comprises:
a housing communicating with the interior of said outer compartment;
a bellows inserted in said housing; and
resilient means coupled to said bellows for holding said bellows within said housing with no pressure in said outer compartment such that a pressure increase in said outer compartment causes said bellows to move out of said housing against the pressure of the resilient means to represent an increase of pressure in said outer compartment.

13. A thermal compress cuff as in claim 12 further comprising reference points marked on said bellows to give an indication of the pressure inside said outer compartment.

14. A device for treating an injured knee of a human limb comprising:
a therapeutic cold and compression applying means including a cuff-like device having a liquid-tight chamber with inner and outer walls and formed with a transverse portion and first and second spaced hollow dependent arms having distal ends, the transverse portion being intended for contact with the general area of only the suprapatella pouch and the first and second hollow arms extending generally along and in contact with the respective sides of the knee;
means for attaching the cold and compression applying means to the knee;
means for applying a pressurized fluid to the cuff-like device; and
means coupled to the compression applying means for limiting the compression applied to the general area alongside and below the knee and no compression behind the knee thereby limiting venous constriction below the knee while simultaneously enabling a different level of compression to be applied to the general area of the suprapatella pouch and independent of the means for attaching the cold and compression applying means to the knee.

15. A device as in claim 14 wherein the means for limiting compression to the areas generally alongside the knee further comprises:
means for restricting expansion of the hollow arms, thereby allowing full compression to be applied by the transverse portion to the general area of the suprapatella pouch and limited compression to be applied by the depending arms to the general area along each side of the knee, in order to lessen venous constriction below the knee.

16. A device as in claim 15 wherein the means for allowing limited compression to be applied to the area generally alongside of the knee comprises;
means in the distal area of each of the arms coupling the inner and outer walls to each other in at least one location to limit the expansion of the arms by limiting the distance the inner and outer chamber walls can move apart when fluid is inserted therein.

17. A device as in claim 16 wherein the means coupling the arm walls together comprises a single tether strip in at least one location coupling the inner and outer walls together to provide restricted expansion of the chamber formed in the arms in the area of the tether strip.

18. A device as in claim 16 wherein the means coupling the arm walls together comprises at least one spot welded area attaching the inner and outer walls together to prevent any expansion of the chamber formed in the arms in the area of the spot weld.

19. A device as in claim 14 further comprising:
a container for holding a liquid; and
means coupling liquid in the container to the liquid tight chamber such that when the container is elevated above the knee, the chamber is inflated with the liquid and compression is supplied to the knee in an amount depending on the level of elevation of the container above the knee and when the container is lowered below the knee, the liquid in the chamber is returned to the container for recooling so as to form a closed system for recirculating the liquid.

20. A device as in claim 14, further comprising:
a middle wall in the chamber for separating the chamber into inner and outer compartments each in a liquid tight relationship;
means coupled to the inner compartment for enabling liquid to be introduced therein for applying cold only to the general suprapatella area and the areas generally alongside the knee; and
means coupled to the outer compartment for permitting a fluid to be introduced in the compartment sufficient to force the inner compartment with its liquid in pressure engagement with the general suprapatella area and the area generally alongside the knee.

21. A device as in claim 20 further comprising pump means coupled to the outer compartment for providing pressurized fluid to the outer compartment.

22. A device as in claim 14 wherein the first and second hollow arms are separated by a triangular shaped open area in the distal end portion and a substantially rectangular area terminating in a semi-circular end at the transverse portion, so as to enable the profile of the cuff-like device to be changed as the knee flexes and to allow more complete conformation of the cuff to the associated knee.

23. A device as in claim 20 further including a syphon system associated with the inner compartment for permitting transfer of the liquid to and from the inner compartment without removing the device from the knee.

24. A device as in claim 14, further comprising:
a middle wall in the chamber for separating the chamber into inner and outer compartments each in a liquid tight relationship;
means coupled to the inner compartment for enabling the liquid to be introduced therein for applying cold only to the general suprapatella area and the areas generally alongside the knee;
means coupled to the outer compartment for permitting a fluid to be introduced in the compartment sufficient to force the inner compartment with its liquid in pressure engagement with the general suprapatella area and the area generally alongside the knee; and
a syphon system associated with the inner compartment for permitting transfer of the liquid to and from the inner compartment without removing the device from the knee, said syphon system comprising a Y-shaped tube extending from an outer end of the inner compartment of one arm to an outer end of the inner compartment of the other of the arms to carry liquid to and receive liquid from outer ends of the arms, a fill opening in the inner compartment, and a connecting tube coupled to the Y-shaped tube and to the fill opening for transfer of fluid to and from the inner compartment through the fill opening.

25. A device for treating an injured knee of a human limb comprising:
a therapeutic cold and compression applying means including a cuff-like device having a liquid-tight chamber with inner and outer walls and formed with a transverse portion and first and second spaced hollow dependent arms, the transverse portion being intended for contact with the general area of only the suprapatella pouch and the first and second hollow arms extending generally along and in contact with the respective sides of the knee;
means for attaching the cold and compression applying means to the knee, said attaching means comprising
(a) a first adjustable inelastic strap attached to one side of the chamber transverse portion and extending to another side of the chamber transverse portion and adapted to be positioned under the leg and above the knee to allow constriction of the leg above the knee;
(b) a second adjustable elastic strap attached to an outer edge of one of the arms and extending to an outer edge of the other arm and adapted to be positioned under the leg and below the knee to limit constriction of the leg below the knee to an amount less than the constriction above the knee; and
(c) a third adjustable strap attached to an inner edge of one of the arms and extending to an inner edge of the other arm and adapted to be positioned over the leg and below the knee;
means for applying a pressurized fluid to the cuff-like device; and
means coupled to the compression applying means for limiting the compression applied to the general area alongside and below the knee and no compression behind the knee thereby limiting venous constriction below the knee while simultaneously enabling a different level of compression to be applied to the general area of the suprapatella pouch and independent of the means for attaching the cold and compression applying means to the knee.

26. A device as in claim 25 further comprising means for inflating and expanding the chamber so as to apply a first compression to the general area of the suprapatella pouch and a second, less compression, to the general area along each side of and below the knee and substantially no pressure behind the knee.

27. A device as in claim 25 wherein at least one of the second and third adjustable straps includes at least a portion that is elastic, thereby to lessen venous constriction of the device below the knee.

28. A thermal compress cuff for treating an injured knee of a limb, said cuff comprising:
a fluid impervious chamber formed of flexible material and having a transverse portion and a pair of arms having distal ends, said arms depending from the transverse portion, the transverse portion adapted to encompass substantially only a portion of the limb above the knee and the depending arms adapted to encompass at least a portion of the limb along the sides of the knee and a portion of the limb below the knee, said arms being separated to expose the patella of the knee;
said chamber being adapted for receiving and containing a thermal fluid for treatment of said knee and for abutting contact with the encompassed portion of the limb;
first means for holding the transverse portion of the chamber in encompassing engagement with substantially only the portion of the limb above the knee so as to allow some constriction of the limb above the knee;
second means for holding the depending arms of the chamber in encompassing engagement with at least a portion of the limb along the sides of and below the knee with the patella being positioned between the depending arms so as to limit constriction of the leg below the knee to an amount less than the constriction above the knee, said second means comprising
(a) a length of strap material attached to and extending transversely inwardly from an inner edge of the distal end of one of the arms and having a length sufficient to pass over the limb below the knee to be releasably secured to the other arm to hold the depending arms in spaced relationship along the sides of and below the knee,
(b) an elongated elastic strap attached to and extending transversely from an outer edge of the distal end of one of the arms for passing under the limb below the knee,
(c) means on the distal end of the other one of said arms for releasably receiving the elongated elastic strap in a fastening relationship as it passed under the limb and below the knee for holding the depending arms snugly against the encompassed area of the limb; and
means independent of the first and second holding means associated with said chamber for applying pressure to the fluid in the chamber.

29. A thermal pressure cuff as in claim 28 wherein the depending arms are separated by a generally triangular shaped area in the distal end portion thereof and a substantially rectangular area extending from the generally triangular shaped area and terminating in a semicircular end at the transverse portion of the cuff so as to enable the cuff to continue to conform substantially to the knee as the knee flexes and so as to allow more complete conformation of the cuff to the limb, and to accommodate limbs of varying sizes.

* * * * *